United States Patent [19]

Nonaka et al.

[11] 4,212,946

[45] Jul. 15, 1980

[54] PROCESS FOR RECOVERING PROTEASE

[75] Inventors: Yuji Nonaka; Kiyotaka Oyama; Heijiro Satoh, all of Shin-nanyo, Japan

[73] Assignees: Toyo Soda Manufacturing Company Limited; (Zaidanhojin) Sagami Chemical Research Center, both of Tokyo, Japan

[21] Appl. No.: 907,203

[22] Filed: May 18, 1978

[30] Foreign Application Priority Data

May 23, 1977 [JP] Japan ................... 52-58828

[51] Int. Cl.$^2$ ........................ C12N 9/48; C07G 7/02
[52] U.S. Cl. .................................. 435/212; 435/213; 435/218; 435/219; 435/225; 435/70; 435/816
[58] Field of Search ............... 195/29, 66 R; 435/212, 435/213, 218, 219, 225

[56] References Cited

U.S. PATENT DOCUMENTS 4,086,136  4/1978  Isowa et al. ............................ 195/29
4,119,493  10/1978 Isowa et al. ............................ 195/29

OTHER PUBLICATIONS

Perlman, Methods in Enzymology, vol. XIX, pp. 646–647, 688–693, 696, 697, 758, 759 and 785 (1970).

Journal of Fermentation Technology 40, 346–353 (1962).
Journal of Biological Chemistry 212, 255–269 (1955).

*Primary Examiner*—Lionel M. Shapiro
*Attorney, Agent, or Firm*—Oblon, Fisher, Spivak, McClelland & Maier

[57] ABSTRACT

Protease is recovered by reacting a first amino acid whose amino group is protected with a protective group with a second amino acid whose carboxyl group is protected with a protective group, in an aqueous medium in the presence of a protease to result a peptide synthesis to deposit the addition compound of a dipeptide and said second C-terminal protected amino acid; dissolving said addition compound by adding an organic solvent to a precipitate separated from the reaction mixture and isolating the protease from an organic solvent suspension or dissolving said addition compound by adding a water immiscible organic solvent and separating the organic solvent phase by a liquid-liquid separation.

The addition compound can be dissolved in an organic solvent after separating the precipitate from the reaction mixture.

The addition compound can be also dissolved by adding a water-immiscible organic solvent to the reaction mixture and the organic solvent phase can be separated from the aqueous phase.

9 Claims, No Drawings

PROCESS FOR RECOVERING PROTEASE

BACKGROUND OF THE INVENTION

1. Field of the Invention

The present invention relates to a process for recovering protease. More particularly, it relates to a process for recovering protease by isolating the protease from a reaction product after a peptide synthesis of peptide-bonding amino acid derivatives in the presence of the protease.

2. Description of Prior Arts

It has been known that proteases such as papain and chymotrypsin are used for forming peptide bonds as the reverse reaction of protein decomposition. For example, anilides have been produced by using papain by Bergman and the peptide syntheses using monoaminocarboxylic acids such as leucine having N-terminal protective benzoyl group and leucine and glycine having C-terminal protective amide or anilide group have been attained with papain and chymotrypsin by Fruton. (Advances in Protein Chemistry Vol. 5, page 33 (1949). Academic Press Inc. New York, N.Y.).

Recently, some of the inventors Isowa et al. reported peptide syntheses using amino acids having an N-terminal protective benzyloxycarbonyl group and amino acids having a C-terminal ester group with enzymes such as papain, Prolisin, Subtilisin BPN' etc. (Nippon Kagakukai 35th Autumn Meeting Brief Report Pages 482 and 486 (1976) Nippon Kagakukai).

Some of the inventors and Isowa et al. proposed the reaction of aspartic acid or glutamic acid having N-terminal protective group with a monoaminomonocarboxylic acid having C-terminal protective group which has no other functional group in the presence of protease whereby an addition compound of the monoaminomonocarboxylic ester having no other functional group and the reaction product was formed, and the isolation of the addition product was carried out. (Japanese Patent Application No. 7279/1977; U.S. patent application Ser. No. 870,108; Canadian patent application No. 295,711 and West German patent application No. P 2801238.6).

The protease used in the process is considered to preserve the protease activity after the reaction. However, the filtrate of the reaction mixture from which the reaction product is separated (The reaction product is deposited to be insoluble in the medium for the reaction.) has only weak protease activity.

According to the studies of the inventors, it has been found that most of the protease used in the reaction is separated together with the reaction product from the filtrate and preserves the protease activity and can be reused for the peptide synthesis etc. after isolating the protease from the reaction mixture.

SUMMARY OF THE INVENTION

It is an object of the present invention to provide a process for recovering protease by isolating protease from a reaction product of a peptide synthesis in the presence of protease.

The foregoing and other objects of the present invention have been attained by providing a process for recovering protease which comprises reacting a first amino acid whose amino group is protected with a protective group with a second amino acid whose carboxyl group is protected with a protective group, in an aqueous medium in the presence of the protease to result a peptide synthesis and to deposit an addition compound of a dipeptide and said second C-terminal protected amino acid; dissolving the addition compound by adding an organic solvent to a precipitate separated from the reaction mixture and isolating the protease from an organic solvent suspension or dissolving said addition compound by adding a water immiscible organic solvent and separating the organic solvent phase by a liquid-liquid separation.

The addition compound can be dissolved in an organic solvent after separating the precipitate from the reaction mixture.

The addition compound can be also dissolved by adding a water-immiscible organic solvent to the reaction mixture and the organic solvent phase can be separated from the aqueous phase.

DETAILED DESCRIPTION OF THE PREFERRED EMBODIMENTS

The addition compounds are disclosed in the copending applications (U.S. patent application Ser. No. 870,108; Canada patent Application No. 295,711 and West German patent application No. P.2801238.6) which are formed by an addition of the second C-terminal protected amino acid with a dipeptide of the first N-terminal protected amino acid and the second C-terminal protected amino acid.

The typical addition compounds have the formula

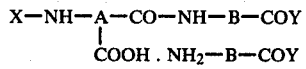

wherein A represents a residue of aspartic acid or glutamic acid excluding C-terminal and N-terminal and B represents a residue of the second amino acid excluding C-terminal and N-terminal and X represents an N-terminal protective group and Y represents a C-terminal protective group.

The proteases recovered by the process of the present invention are proteases used for peptide syntheses.

Suitable proteases include acidic proteases such as pepsin; thiol proteases such as papain, Stembromelein, Ficin, Cathepsin B, Chymopapain and Streptoccal proteases; metallo proteases such as neutral proteases derived from actinomycetes, Prolisin, Thermolysin, Collagenase, Crotulus atrox protease; and serine proteases such as Subtilisin, Aspergillus alkaline proteases. Elastase, α-Lytic protease, Chymotrypsin and Chymotrypsin C.

It is especially suitable to use metallo proteases from the viewpoints of suitable pH range and suitable esterase activity in the preparation of the addition compounds.

The first amino acid whose amino group is protected with a protective group can be an amino acid such as aspartic acid, glutamic acid, whose amino group is protected with the protective group such as an aliphatic oxycarbonyl group, benzyloxycarbonyl group which can have substituents on the ring, benzoyl group, an aromatic sulfonyl group or an aromatic sulfinyl group.

Aspartic acid whose amino group is protected with benzyloxycarbonyl group, or alkoxybenzyloxycarbonyl group especially methoxybenzyloxycarbonyl group and glutamic acid whose amino group is protected with said group are especially important as the starting material.

The second amino acid whose carboxyl group is protected with a protective group can be an amino acid such as glycine, alanine, valine, leucine, isoleucine, phenylalanine, methionine, cystine (cysteine) serine, threonine, aspartic acid, glutamic acid, lysine, arginine, histidine, proline, oxyproline, tyrosine and triptophan and whose carboxyl group is protected with the protective group such as an lower alkoxy group, benzyloxy group, benzhydryloxy group, anilino group or amido group.

Monoaminomonocarboxylic acids having no other functional group such as lower alkyl esters of phenylalanine are especially important as the starting material.

The amounts (concentrations) of these starting materials are not critical, and usually the ranges proposed in the prior inventions. For example, these starting materials are used as solutions having each concentration of about 0.001 M to 7 M.

In the prior invention, the ratio of the first starting material to the second starting material is a molar ratio of 1:2.

The molar ratio of the starting materials used in the practical operation is not critical, and usually in a range of about 5:1 to 1:5 preferably about 2:1 to 1:3.

The aqueous medium is usually water. It is possible to combine a water miscible organic solvent if the protease is not precipitated and the precipitation of the reaction product is not prevented by the addition of the water miscible organic solvent.

The amount of the protease can be the same with the amount of the protease used in the prior invention and usually in a range of about 2 to 400 mg ($5 \times 10^{-5}$ to $1 \times 10^{-2}$ mmole) especially 5 to 100 mg ($1 \times 10^{-4}$ to $3 \times 10^{-3}$ mmole) per 1 mmole of the starting material.

The pH of the aqueous medium in the reaction is in a range for imparting the protease activity and imparting the protease activity and performing the formation reaction of the addition compound, usually about 4 to 9.

The reaction temperature is in a range for maintaining the protease activity and preferably about 20° to 50° C.

The reaction time is not critical and preferably about 30 minutes to 24 hours.

In the process of the present invention, the solubility of the addition compound to the aqueous medium is relatively low whereby the reaction product is deposited.

In the case of the prior invention wherein the first component is aspartic acid or glutamic acid whose amino group is protected and the second component is a monoaminomonocarboxylic acid having no other functional group whose carboxyl group is protected with a lower alkoxy group, the precipitates are the addition compounds of the second component with the dipeptide having the first and second components at a molar ratio of 1:1.

When the solid-liquid separation of the suspension is carried out, the addition compound can be separated as the solid phase wherein the protease having the protease activity is contained.

The solid-liquid separation can be carried out by the conventional methods such as the centrifugal separation and the filtration.

When the organic solvent is added to the resulting solid phase, the addition compound is dissolved in the organic solvent whereas the protease is suspended in the solution.

The solid phase obtained by the solid-liquid separation can be washed with water or the other solvent or dried before the addition of the organic solvent.

The organic solvent added for the addition compounds can be chlorinated lower hydrocarbons such as chloroform, methylenedichloride or ethylenedichloride; esters such as ethyl acetate; alcohols such as methanol, ethanol or propanol; ketones such as acetone and oxygen-containing solvents such as tetrahydrofuran etc.

The amount of the organic solvent is depending upon the solubility to dissolve the precipitate and usually more than 10 wt. parts preferably in a range of 20 to 100 wt. parts per 1 wt. part of the precipitate.

When an organic solvent which is immiscible to water is added to the aqueous suspension of the precipitate, the addition compound is dissolved in the organic solvent whereas the protease is not dissolved in an organic solvent.

The organic solvents which are immiscible to water can be chloroform, methylenedichloride, ethylenedichloride, ethyl acetate etc.

The amount of the organic solvent is suitable for the liquid-liquid extraction, and it is usually in a range of about 1 to 50 wt. parts preferably 2 to 20 wt. parts per 1 wt. part of the aqueous medium.

The volumetric change of the organic solvent can be considered by natural dissolution to water. In said case, the amount of the organic solvent is considered from the viewpoint of the volumetric change or the organic solvent saturated with water is used.

When a medium which is different from water is included, it is necessary to take care of preventing the formation of the two separate phases under partitions to water and to the organic solvent.

The organic solvent phase can be separated from the water phase by the conventional method.

The addition compound can be easily obtained from the separated organic solvent phase by the conventional methods such as the distillation of the organic solvent or the back-extraction from an aqueous solution after adjusting pH.

The separated water phase contains the protease having the protease activity (sometimes it is a suspension), whereby the water phase can be used for the peptide synthesis or the other protease.

The separated water phase contains the protease having the protease activity (sometimes, it is a suspension), whereby the water phase can be used for the peptide synthesis or the other protease reaction, if necessary, after removing impurities by suitable method such as a dialysis. It is also possible to separate the protease from the aqueous solution by suitable method such as the salting-out.

In the other embodiment, the addition compound precipitated by the reaction is separated from the aqueous solution and if necessary, the precipitate is washed with water or the other liquid and then, the water immiscible organic solvent is added to dissolve the reaction product in the organic solvent whereas the protease is dissolved in the water phase and then, the reaction product and the protease are recovered as described above.

The amount of the organic solvent is the same with the above case and it is more than that of dissolving the reaction product.

The amount of the organic solvent is depending upon the solubility to dissolve the precipitate and usually in a range of 5 to 200 wt. parts, preferably 10 to 100 wt. parts per 1 wt. part of the precipitate.

The amount of water can be that of forming two phases of the water phase and the organic solvent phase, and it is usually the amount of water used in the usual liquid-liquid extraction and it is to give the organic solvent in a range of about 1 to 50 wt. parts, preferably about 2 to 20 wt. parts (after saturation with water) per 1 wt. part of water.

It is not economical to use a large amount of water since a concentration of the protease is low. When the amount of water is small, a part of the protease is remained as the suspension, but it does not cause trouble.

In the latter case, the precipitate can be separated from most of the aqueous medium. Accordingly, even though the other medium is included together with water in the aqueous medium, it is not necessary to consider the effect in the step of the recovery of the protease.

The temperature in the step of dissolving the precipitate by adding the water miscible polar organic solvent is the range for preventing the inactivation of the protease and usually about $-20°$ to $50°$ C. preferably about $-10°$ to $30°$ C.

It is necessary to take care of preventing the freezing of the reaction mixture.

The protease is isolated as the solid phase by suitable solid-liquid separation of the resulting suspension.

The solid-liquid separation can be the conventional methods such as the filtration, the centrifugal separation etc.

It is possible to use a filter acid.

The addition compound can be obtained from the separated liquid phase by the conventional methods for example the method of distilling off the organic solvent and then, extracting it with suitable solvent.

The recovered protease maintains the protease activity whereby it can be used for the peptide synthesis and others.

In accordance with the process of the present invention, the recovery and the reuse of the protease can be attained. The cost of the protease is important for the total cost of the peptide synthesis.

The invention will be further illustrated by certain examples.

EXAMPLE 1

In a 30 ml flask, 0.534 (2 m mole) of N-benzyloxycarbonyl-L-aspartic acid and 0.863 g (4 m mole) of L-phenylalanine methyl ester hydrochloride were charged and 5 ml of water was added to dissolve them and pH was adjusted to 6.4 with 7% ammonia water.

The resulting solution was admixed with 30 mg of Thermolysin and shaken at $38°$ to $40°$ C. for 2.5 hours to react them and the precipitate was collected by a filtration and washed with 10 ml of water, and 60 ml of acetone was added. The precipitated reaction product which was cooled with ice was dissolved in acetone phase and the mixture was kept for 40 minutes. The insoluble material was isolated by a centrifugal sedimentation. The protease activity was measured by the casein digestion method. As the result, a relative protease activity of the isolated insoluble material (recovered Thermolysin) to 30 mg of the original Thermolysin was 0.64.

In the following examples, the relative protease activity was measured by the casein digestion method otherwise specified.

On the other hand, acetone was distilled off from the isolated liquid phase at $50°$ to $60°$ C. under a reduced pressure and the residue was cooled to the room temperature whereby crystals were deposited.

The crystals were filtered and washed with 10 ml of water and dried to obtain 0.764 g of fine needle-like crystals which was confirmed to be an addition compound of N-benzyloxycarbonyl-L-aspartyl-L-phenylalanine methyl ester and L-phenylalanine methyl ester (1:1) (yield: 70%).

The crystals were recrystallized from a solvent mixture of ethyl acetate and n-hexane. The physical properties and result of elementary analysis of the product were as follows.

Melting point: $120°$ to $124°$ C.

$[\alpha]_D^{25}$: +7.1 (C=1, methanol).

| Elementary analysis: $C_{32}H_{37}N_3O_9$ | | | |
|---|---|---|---|
| | C | H | N |
| Calculated (%) | 63.24 | 6.13 | 6.97 |
| Found (%) | 63.31 | 6.19 | 7.01 |

Infrared and NMR spectra of the product were as follows.

Infrared spectrum: $3,260^{cm-1}$ (N—H stretching vibration); 3,000 to $3,200^{cm-1}$ (C—H stretching vibration); $1,740^{cm-1}$ (C=O ester); $1,720^{cm-1}$ (C=O urethane); $1,660^{cm-1}$ (amide 1st absorption); $1,630^{cm-1}$ (carboxylate); $1,540^{cm-1}$ (amide 2nd absorption); 1,430 and $1,450^{cm-1}$ (C—H deformation vibration); $1,390^{cm-1}$ (carboxylate); 1,220 to $1,290^{cm-1}$ (C—O—C stretching vibration and amide 3rd absorption); $1,050^{cm-1}$ (phenyl in-plane vibration); and 740 and $695^{cm-1}$ (monosubstituted benzene ring out-of-plane vibration).

NMR spectrum: $\delta$=2.75 ppm; 3.02 ppm; 3.61 ppm; 3.7 ppm; 4.4–4.8 ppm; 5.05 ppm; 5.82 ppm; 7.3 ppm.

EXAMPLE 2

In accordance with the process of Example 1 except using 3.5 ml of water for dissolving N-benzyloxycarboxyl-L-aspartic acid and L-phenylalanine methyl ester hydrochloride and using 50 mg of Thermolysin, the reaction and the isolation of the protease were carried out.

The reaction and the isolation of the protease were repeated by using the isolated insoluble material instead of 50 mg of Thermolysin.

On the other hand, a test sample was prepared by adding L-aspartic acid $\beta$-benzyl ester to the filtrate of the acetone solution as the internal standard substance and the yield of the addition compound of N-benzyloxycarbonyl-L-aspartyl-L-phenylalanine methyl ester and L-phenylalanine methyl ester (1:1) was measured by the high speed liquid chromatography analysis to give 81.0% at the first time and 57.2% at the second time.

The apparatus and conditions in the high speed liquid chromatography analysis are as follows.

Apparatus: High speed liquid chromatography apparatus (TSK-HLC 801 manufactured by Toyo Soda Industrial Co. Ltd.);

Column: Starch gel type: particle size of 5μ. (TSK-GEL LS 170 manufactured by Toyo Soda Industrial Co., Ltd.);

Eluent: 0.5% aqueous solution of sodium acetate:

Flow rate: 0.8 ml/min.;

Pressure loss: 20 Kg/cm²;

Detector: Differential refractometer.

In the following examples, the yields of the products were measured by using the same apparatus under the same condition otherwise specified.

EXAMPLE 3

In 4 ml of water, 400 mg of Thermoase (titer 1,600,000 PU PU/g) was dissolved and the insoluble material was separated by the centrifugal sedimentation, and 60 mg of potato inhibitor was added to 3.0 ml of the supernatant and the mixture was kept for 15 minutes.

In accordance with the process of Example 2, except using 2.5 ml of resulting solution instead of 50 mg of Thermolysin, the reaction and the isolation of the protease were carried out.

The reaction and the isolation were repeated except using the recovered protease instead of said solution of the protease.

The yield of the addition compound of N-benzyloxycarbonyl-L-aspartyl-L-phenylalanine methyl ester and L-phenylalanine methyl ester (1:1) was 79.1% at the first time and 59.3% at the second time.

EXAMPLE 4

In accordance with the process of Example 1 except using 3.5 ml of water for dissolving N-benzyloxycarboxyl-L-aspartic acid and L-phenylalanine methyl ester hydrochloride and using 50 mg of Thermolysin, the reaction was carried out. The precipitate of the reaction product was filtered and washed with water.

In accordance with the process of Example 1 except using 50 ml of tetrahydrofuran instead of 60 ml of acetone, the isolations of the protease and the reaction product were carried out.

The relative protease activity of the recovered protease to 50 mg of the original Thermolysin was 0.60.

The yield of the addition compound of N-benzyloxycarbonyl-L-aspartyl-L-phenylalanine methyl ester and L-phenylalanine methyl ester (1:1) was 77.3%.

EXAMPLE 5

The process of Example 4 was repeated except using 100 ml of ethyl acetate instead of 50 ml of tetrahydrofuran.

The relative protease activity of the recovered protease to 30 mg of the original Thermolysin was 0.52.

The yield of the addition compound of N-benzyloxycarbonyl-L-aspartyl-L-phenylalanine methyl ester and L-phenylalanine methyl ester (1:1) was 86.4%.

EXAMPLE 6

In a 30 ml flask, 0.563 g (2 m mole) of N-benzyloxycarbonyl-L-glutamic acid and 0.863 g (4 m mole) of L-phenylalanine methyl ester hydrochloride were charged and 35 ml of water was added to dissolve them and pH was adjusted to 6.3 with 1 N-NaOH aqueous solution.

The resulting solution was wixed with 50 mg of Thermolysin and the mixture was stirred at 38° to 40° C. for 21 hours to react them. The precipitate of the reaction product was filtered and washed with 10 ml of water and dissolved in 60 ml of acetone cooling with ice, and the mixture was kept for 40 minutes. The insoluble material was isolated by a centrifugal sedimentation.

The relative protease activity of the insoluble material to 50 mg of the original Thermolysin was 0.30.

In accordance with the process of Example 1, the isolated acetone solution was treated to obtain 0.758 g (yield 61%) of crude crystals of an addition compound of N-benzyloxycarbonyl-L-glutamyl-L-phenylalanine methyl ester and L-phenylalanine methyl ester (1:1).

The physical properties and the result of the elementary analysis of the product obtained by recrystallizing from a mixed solvent of ethyl acetate and n-hexane were as follows.

Melting point: 92° to 97° C.
$[\alpha]_D^{25}$: 0.1 (C=1 methanol).

| Elementary analysis: $C_{33}H_{39}N_3O_9$ | | |
|---|---|---|
| | C | H | N |
| Calculated (%) | 63.75 | 6.32 | 6.75 |
| Found (%) | 63.79 | 6.29 | 6.68 |

Infrared spectrum: $3,340^{cm-1}$ (N—H stretching vibration); 2,950 and $3,030^{cm-1}$ (C—H stretching vibration); 1,730 and $1,745^{cm-1}$ (C=O ester); $1,690^{cm-1}$ (C=O urethane); $1,660^{cm-1}$ (amide 1st absorption); $1,620^{cm-1}$ (carboxylate); $1,530^{cm-1}$ (amide 2nd absorption); $1,440^{cm-1}$ (C—H deformation vibration); $1,405^{cm-1}$ (carboxylate); 1,240 to $1,310^{cm-1}$ (C—O—C stretching vibration and amide 3rd absorption); $1,050^{cm-1}$ (phenyl in-plane vibration); 700 and $750^{cm-1}$ (phenyl out-of-plane vibration).

| NMR spectrum: | | |
|---|---|---|
| δ 2.0 ppm (2H); | 2.3 ppm (2H); | |
| 3.0 ppm (4H); | 3.6 ppm (3H) | 3.7 ppm (3H); |
| 3.8 ppm (1H); | 4.3 ppm (1H); | |
| 4.8 ppm (1H); | 5.0 ppm (2H); | |
| 5.8 ppm (3H); | 5.8 ppm (1H); | |
| 7.2 ppm (1H); | 7.2 ppm (10H); | |
| 7.3 ppm (5H). | | |

EXAMPLE 7

The reaction of Example 2 was repeated except adjusting pH to 6.0 with 1N-NaOH aqueous solution. The precipitate of the reaction product was filtered and washed with 10 ml of water and dried at the room temperature in vacuum for 30 minutes. Then 30 ml of methylenedichloride was added to dissolve it under cooling with ice. After 30 minutes, the precipitate was filtered to recover the protease. The relative protease activity of the recovered protease to 50 mg of the original Thermolysin was 0.50.

The yield of the addition compound of N-benzyloxycarbonyl-L-aspartyl-L-phenylalanine methyl ester and L-phenylalanine methyl ester (1:1) was 77.2%.

EXAMPLE 8

In a 30 ml flask, 0.534 (2 m mole) of N-benzyloxycarbonyl-L-aspartic acid and 0.863 g (4 m mole) of L-phenylalanine methyl ester hydrochloride were charged and 5 ml of water was added to dissolve them and pH was adjucsted to 6.4 with 7% ammonia water.

The resulting solution admixed with 30 mg of Thermolysin and shaken at 38° to 40° C. for 2.5 hours to react them and 20 ml of chloroform was added to the reaction mixture containing the precipitated reaction product at the room temperature and the mixture was kept to form two phases.

The two phases were separated. The protease activity of the water phase was measured by the casein digestion method. As the result, a relative protease activity of the water phase to 30 mg of the original Thermolysin was 0.64.

On the other hand, chloroform was distilled off from the isolated organic phase at 50° to 60° C. under a reduced pressure.

The crystals were filtered and washed with 10 ml of water and dried to obtain 0.802 g of fine needle-like crystals which was confirmed to be addition compound of N-benzyloxycarbonyl-L-aspartyl-L-phenylalanine methyl ester and L-phenylalanine methyl ester (1:1) (yield: 66%).

The crystals were recrystallized from a solvent mixture of ethyl acetate and n-hexane. The physical properties and result of elementary analysis of the product were as follows.

Melting point: 120° to 124° C.
$[\alpha]_D^{25}$: +7.1 (C=1, methanol).

| Elementary analysis: $C_{32}H_{37}N_3O_9$ | | | |
|---|---|---|---|
| | C | H | N |
| Calculated (%) | 63.24 | 6.13 | 6.97 |
| Found (%) | 63.28 | 6.11 | 7.01 |

EXAMPLE 9

In accordance with the process of Example 8 except using 53 mg of Thermolysin and reacting them for 130 minutes and using 35 ml of chloroform, the reaction, the formation of two phases and the isolation of the protease were carried out.

The reaction and the isolation were repeated except using the water phase instead of 53 mg of Thermolysin.

The yield of the addition compound of N-benzyloxycarbonyl-L-aspartyl-L-phenylalanine methyl ester and L-phenylalanine methyl ester (1:1) was 83.8% at the first time and 24.6% at the second time.

EXAMPLE 10

In accordance with the process of Example 8, the reaction was carried out. After the reaction, 20 ml of water was added to the reaction mixture and 20 ml of methylene chloride was added and the mixture was shaken and kept to form two phases and the two phases were separated.

A relative protease activity of the water phase to 30 mg of the original Thermolysin was 0.60.

The yield of the addition compound of N-benzyloxycarbonyl-L-aspartyl-L-phenylalanine methyl ester and L-phenylalanine methyl ester (1:1) was 68.3%.

EXAMPLE 11

In accordance with the process of Example 8 except using 50 mg of Thermolysin, the reaction was carried out. After the reaction, 15 ml of water was added to the reaction mixture and 80 ml of ethylenedichloride was added and the mixture was shaken and kept to form two phases, and the two phases were separated.

The relative enzyme activity of the water phase to 50 mg of the original Thermolysin was 0.40.

The yield of the addition compound of N-benzyloxycarbonyl-L-aspartyl-L-phenylalanine methyl ester and L-phenylalanine methyl ester (1:1) was 74.1%.

EXAMPLE 12

The process of Example 11 was repeated except using 100 ml of ethyl acetate instead of 80 ml of ethylenedichloride.

The realtive protease activity of the water phase to 50 mg of the original Thermolsin was 0.64.

The yield of the addition compound of N-benzyloxycarbonyl-L-aspartyl-L-phenylalanine methyl ester and L-phenylalanine methyl ester (1:1) was 65.1%.

EXAMPLE 13

The process of Example 11 was repeated except using 100 ml of diethyl ketone instead of 80 ml of ethylenedichloride.

The relative protease activity of the water phase to 50 mg of the original Thermolysin was 0.46.

The yield of the addition compound of N-benzyloxycarbonyl-L-aspartyl-L-phenylalanine methyl ester and L-phenylalanine methyl ester (1:1) was 71.0%.

EXAMPLE 14

In a 30 ml flask, 0.563 g (2 m mole) of N-benzyloxycarbonyl-L-glutamic acid and 0.863 g (4 m mole) of L-phenylalanine methyl ester hydrochloride were charged and 5 ml of water was added to dissolve them and pH was adjusted to 6.1 with 1N-NaOH aqueous solution.

The resulting solution was mixed with 50 mg of Thermolysin and the mixture was stirred at 38° to 40° C. for 21 hours to react them and 20 ml of methylenedichloride was added to the reaction mixture which was cooled with ice and the mixture was kept for 30 minutes to form two phases.

The two phases were separated. The methylenedichloride phase was mixed with 5 ml of water and the mixture was shaken and kept in cooling with ice for 20 minutes and the two phases were separated.

The resulting two water phases were mixed, and the protease activity was measured.

The realtive protease activity of the water phases to 50 mg of the original Thermolysin was 0.90.

On the other hand, methylenedichloride was distilled off from the methylenedichloride phase and the residual crystals were washed with 10 ml of water and dried to obtain 0.584 g (yield: 47%) of crude crystals of an addition compound of N-benzyloxycarbonyl-L-glutamyl-L-phenylalanine methyl ester and L-phenylalanine methyl ester (1:1).

The physical properties and the result of elementary analysis of the product obtained by recrystallizing from a mixed solvent of ethyl acetate and n-hexane were as follows.

Melting point: 91° to 96° C.
$[\alpha]_D^{25}$: 0.1 (C=1 methanol).

| Elementary analysis: $C_{33}H_{39}N_3O_9$ | | | |
|---|---|---|---|
| | C | H | N |
| Calculated (%) | 63.75 | 6.32 | 6.75 |
| Found (%) | 63.81 | 6.38 | 6.71 |

EXAMPLE 15

In accordance with the process of Example 1, the reaction was carried out. The precipitated reaction product was filtered and washed with 20 ml of water, and then, dissolved in 20 ml of chloroform at the room temperature, and 30 ml of water was added to it. The mixture was shaken and kept to form two phases, and the two phases were separated.

The relative protease activity of the water phase to 30 mg of the original Thermolysin was 0.44.

The yield of the addition compound of N-benzyloxycarbonyl-L-aspartyl-L-phenylalanine methyl ester and L-phenylalanine methyl ester (1:1) was 63.7%.

What is claimed is:

1. A process for recovering protease which comprises reacting a first amino acid whose amino group is protected with a protective group with a second amino acid whose carboxyl group is protected with a protective group in an aqueous medium in the presence of the protease to result in a peptide synthesis and to deposit as a precipitate the addition compound of a dipeptide and said second C-terminal protected amino acid; dissolving said addition compound by adding an organic solvent to a precipitate separated from the reaction mixture and isolating the protease from said organic solvent.

2. A process according to claim 1 wherein the protective group for the amino group of the first amino acid or peptide is an aliphatic oxycarbonyl group, a benzloxycarbonyl group which can have ring substituents, a benzoyl group, an aromatic sulfonyl group or an aromatic sulfuryl group; and the protective group for the carboxyl group of the second amino acid or peptide is a lower alkoxy group or a benzhydryloxy group.

3. A process according to claim 1 wherein the protease is a metallo protease.

4. A process according to claim 1 wherein the precipitate is the addition compound having the formula

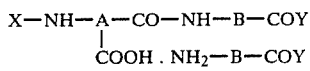

wherein A represents a residue of asparatic acid or glutamic acid exluding C-terminal and N-terminal and B represents a residue of the second amino acid excluding C-terminal and N-terminal and X represents an N-terminal protective group and Y represents a C-terminal protective group.

5. A process according to claim 1 wherein the first amino acid is asparatic acid or glutamic acid and the second amino acid or peptide is a monoaminomonocarboxylic acid having no other functional group.

6. A process according to claim 1 wherein the monoaminomonocarboxylic acid having no other functional group is phenylalanine.

7. A process according to claim 1 wherein the aqueous medium is water.

8. A process for recovering protease which comprises reacting a first amino acid whose amino group is protected with a protective group with a second amino acid whose carboxyl group is protected with a protective group in an aqueous medium in the presence of the protease to result in a peptide synthesis and to deposit as a precipitate the addition compound of a dipeptide and said second C-terminal protected amino acid; dissolving said precipitate by adding a water immiscible organic solvent to said aqueous medium; separating the resulting organic phase from the aqueous phase; and separating said protease from said aqueous phase.

9. A process according to claim 8, wherein the protective group for the amino group of the first amino acid or peptide is an aliphatic oxycarbonyl group, a benzyloxycarbonyl group which can have ring substituents, a benzoyl group, an aromatic sulfonyl group or aromatic sulfuryl group; and the protective group for the carboxyl group of the second amino acid or peptide is lower alkoxy group or a benzhydryloxy group.

* * * * *

UNITED STATES PATENT AND TRADEMARK OFFICE
CERTIFICATE OF CORRECTION

PATENT NO. : 4,212,946

DATED : July 15, 1980

INVENTOR(S) : YUJI NONAKA ET AL

It is certified that error appears in the above—identified patent and that said Letters Patent is hereby corrected as shown below:

Column 7, line 55, delete "wixed" and insert --mixed--.

Column 9, line 6, after "be" insert --an--;

line 67, delete "realtive" and insert --relative--.

Column 10, line 35, delete "realtive" and insert --relative--.

Columns 11-12, delete Claims 2-8 in their entirety and insert the following:

--2. A process for recovering protease which comprises reacting a first amino acid whose amino group is protected with a protective group with a second amino acid whose carboxyl group is protected with a protective group in an aqueous medium in the presence of the protease to result in a peptide synthesis and to deposit as a precipitate the addition compound of a dipeptide and said second C-terminal protected amino acid; dissolving said precipitate by adding a water immiscible organic solvent to said aqueous medium; separating the resulting organic phase from the aqueous phase; and separating said protease from said aqueous phase.

3. A process according to Claim 1, wherein the protective group for the amino group of the first amino acid or peptide is an aliphatic oxycarbonyl group, a benzyloxycarbonyl group which can have ring substituents, a benzoyl group, an aromatic sulfonyl group or an aromatic

UNITED STATES PATENT AND TRADEMARK OFFICE
CERTIFICATE OF CORRECTION

PATENT NO. : 4,212,946
DATED : July 15, 1980
INVENTOR(S) : YUJI NONAKA ET AL

It is certified that error appears in the above—identified patent and that said Letters Patent is hereby corrected as shown below:

sulfuryl group; and the protective group for the carboxyl group of the second amino acid or peptide is a lower alkoxy group or a benzhydryloxy group.

4. A process according to Claim 1 or 2, wherein the protease is a metallo protease.

5. A process according to Claim 1 or 2, wherein the precipitate is the addition compound having the formula

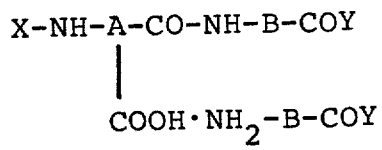

wherein A represents a residue of aspartic acid or glutamic acid excluding C-terminal and N-terminal and B represents a residue of the second amino acid excluding C-terminal and N-terminal and X represents an N-terminal protective group and Y represents a C-terminal protective group.

6. A process according to Claim 1 or 2, wherein the first amino acid is aspartic acid or glutamic acid and the second amino acid or peptide is a monoaminomonocarboxylic acid having no other functional group.

7. A process according to Claim 6, wherein the monoaminomonocarboxylic acid having no other functional

UNITED STATES PATENT AND TRADEMARK OFFICE
CERTIFICATE OF CORRECTION

PATENT NO. : 4,212,946  
DATED : July 15, 1980  
INVENTOR(S) : YUJI NONAKA ET AL Page 3 of 3

It is certified that error appears in the above—identified patent and that said Letters Patent is hereby corrected as shown below:

group is phenylalanine.

8. A process according to Claim 1 or 2, wherein the aqueous medium is water.--

Column 12, in Claim 9, first line, delete "8" and insert --2--.

Signed and Sealed this

Nineteenth Day of May 1981

[SEAL]

Attest:

RENE D. TEGTMEYER

Attesting Officer     Acting Commissioner of Patents and Trademarks